United States Patent [19]
Cinberg et al.

[11] Patent Number: 5,489,286
[45] Date of Patent: Feb. 6, 1996

[54] ANTIBIOTIC IMPREGNATED MYRINGOTOMY VENTILATION TUBE

[76] Inventors: James Z. Cinberg, 167 N. Ridgewood Rd., South Orange, N.J. 07079; Peter J. Wilk, 185 W. End Ave., New York, N.Y. 10023

[21] Appl. No.: 221,486

[22] Filed: Apr. 1, 1994

Related U.S. Application Data

[63] Continuation-in-part of Ser. No. 60,811, May 12, 1993, abandoned, which is a continuation-in-part of Ser. No. 959,672, Oct. 13, 1992, Pat. No. 5,254,120, which is a continuation-in-part of Ser. No. 921,308, Jul. 28, 1992, Pat. No. 5,207,685.

[51] Int. Cl.⁶ ..................................................... A61F 11/00
[52] U.S. Cl. ............................................................. 606/109
[58] Field of Search .......................... 606/1, 109; 604/164, 604/264, 265

[56] References Cited

U.S. PATENT DOCUMENTS

| | | |
|---|---|---|
| 3,530,860 | 9/1970 | Majoros . |
| 3,871,380 | 3/1975 | Heros . |
| 3,888,258 | 6/1975 | Akiyama . |
| 3,897,786 | 8/1975 | Garnett et al. . |
| 3,948,271 | 4/1976 | Akiyama . |
| 3,982,545 | 9/1976 | Silverstein . |
| 4,168,697 | 9/1979 | Cantekin . |
| 4,605,564 | 8/1986 | Kulla et al. ............................. 604/265 |
| 4,650,488 | 3/1987 | Bays et al. ............................. 604/265 |
| 4,764,168 | 8/1988 | Suh . |
| 4,775,370 | 10/1988 | Berry . |
| 4,863,444 | 9/1989 | Blömer ................................... 604/265 |
| 4,971,076 | 11/1990 | Densert et al. . |
| 5,013,306 | 5/1991 | Solomon et al. ....................... 604/265 |
| 5,026,378 | 6/1991 | Goldsmith . |
| 5,047,053 | 9/1991 | Jahn . |
| 5,053,040 | 10/1991 | Goldsmith . |
| 5,165,952 | 11/1992 | Solomon et al. ....................... 604/265 |
| 5,217,493 | 6/1993 | Raad et al. ............................. 604/265 |

FOREIGN PATENT DOCUMENTS 1326276  7/1987  U.S.S.R. .

Primary Examiner—Stephen C. Pellegrino
Assistant Examiner—Glenn Dawson
Attorney, Agent, or Firm—R. Neil Sudol; Henry D. Coleman

[57] ABSTRACT

A tympanic ventilation tube or pressure equalization device includes a pair of flanges disposed at opposite ends of a tubular member. At least one of the tubular member and the flanges is made of a polymeric material impregnated with an antibiotic.

19 Claims, 6 Drawing Sheets

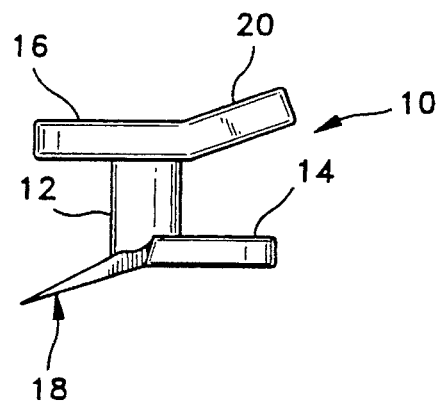
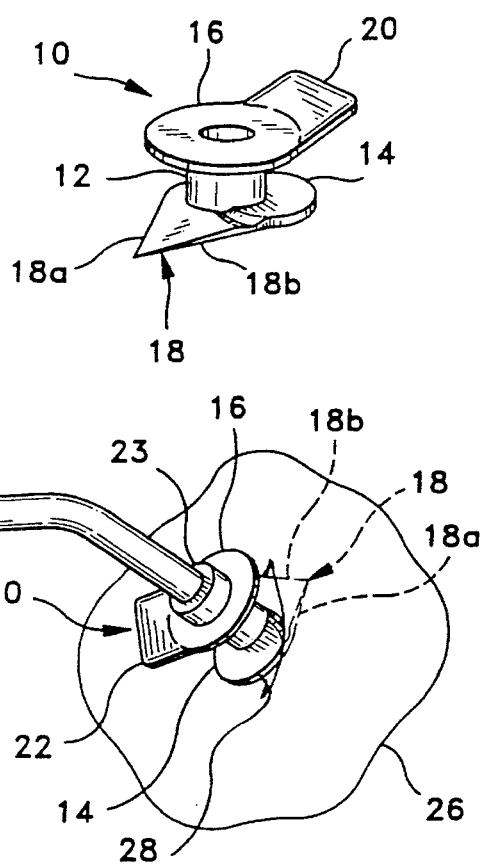
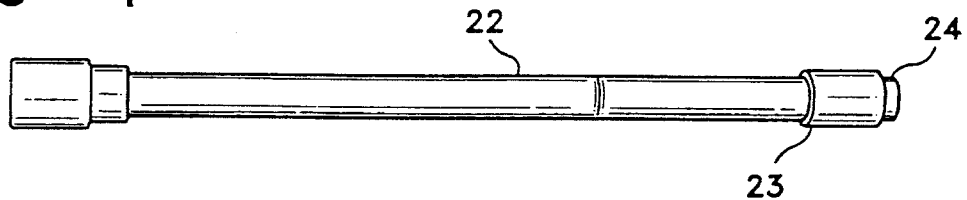
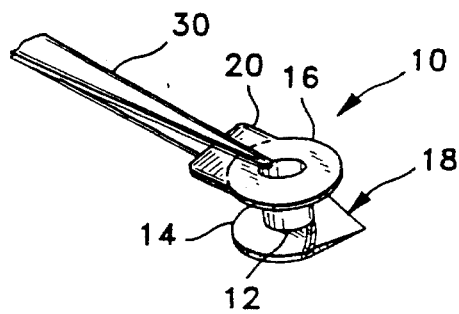
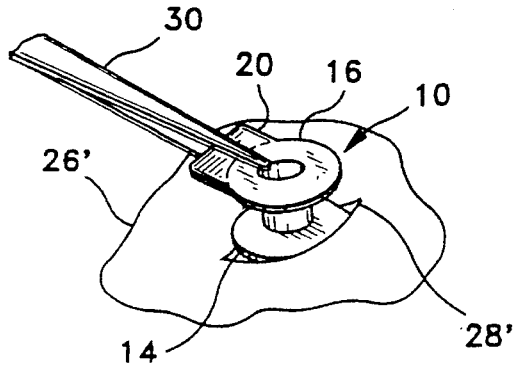

5,489,286

ANTIBIOTIC IMPREGNATED MYRINGOTOMY VENTILATION TUBE

Cross-Reference to Related Applications

This application is a continuation-in-part of application Ser. No. 08/060,811 filed May 12, 1993, abandoned, which is a continuation-in-part of application Ser. No. 07/959,672, now U.S. Pat. No. 5,254,120, which was filed Oct. 13, 1992 which is a continuation-in-part of application Ser. No. 921,308 filed Jul. 28, 1992, now U.S. Pat. No. 5,207,685.

FIELD OF THE INVENTION

This invention relates to a ventilation tube which is placed in a patient's tympanic membrane for purposes of pressure equalization between the middle ear cleft and the ambient atmospheric pressure and also for draining fluid from the middle ear.

BACKGROUND OF THE INVENTION

Children frequently have an abnormal condition characterized by fluid in the middle ear cleft. A myringotomy or tympanostomy with placement of a ventilation or pressure equalization tube is a surgical operation performed on the ear drum to drain the fluid and ventilate the middle ear for a longer period than would be possible with only an incision of the ear drum as spontaneous drum closure occurs in a week or two after the incision of the ear drum: a result of standard repair processes of an incised ear drum. During a myringotomy and tube placement, as conventionally performed, an ear knife cuts the ear drum and creates an incision. Complications of this procedure are inadvertant laceration of the external ear canal as the knife moves towards or away from the drum and creation of a drum incision which is either too short or too long. Then a ventilation tube is inserted through the incision and manipulated to remain seated in the incision, thereby providing a duct or channel for draining fluid from the middle ear and ventilating the middle ear space via the external auditory canal.

During insertion down into the external auditory canal and placement in the tympanic membrane, the ventilation tube is held by a special grasping forceps. Because the ventilation tube is so tiny and the ear drum so delicate, a myringotomy and tube placement is an especially sensitive operation and gives rise to considerable challenges to a surgeon's dexterity and patience.

OBJECTS OF THE INVENTION

An object of the present invention is to provide an improved ventilation or pressure equalization tube for use in ventilating and/or draining fluid from the middle ear.

A more particular object of the present invention is to provide a ventilation or pressure equalization tube which reduces the chances of infection of the tympanic membrane and in the middle ear cleft.

These and other objects of the present invention will be apparent from the descriptions and illustrations herein.

SUMMARY OF THE INVENTION

A device for releasing fluid from the middle ear comprises, in accordance with the present invention, a tubular member, a proximal flange at one end of the tubular member and a distal flange at an opposite end of the tubular member. At least one of the tubular member, the proximal flange and the distal flange is made of a polymeric material impregnated with an antibiotic. Upon implantation or insertion of the pressure equalization tube in a tympanic membrane of a patient, the antibiotic diffuses outwardly into the tympanic tissues and/or the middle ear cleft to reduce, if not eliminate, the chance of infection.

The antibiotic may be taken from the amino glycocide family, e.g., gentamycin or tobramycin, from the ciprofloxacin family, or from the cephalosporin family. In the embodiments of FIGS. 9 through 18, the entire ventilation tube may be made of a polymeric material impregnated with an antibiotic.

Pursuant to one embodiment of the present invention, a blade member is removably attached to the tubular member at one end thereof, e.g., at the proximal end. More particularly, the blade member is attached to the proximal flange by being seated in a groove provided in that flange. The blade member facilitates the incising of a tympanic membrane during an insertion of the tubular member, wherein the flanges seat against opposite sides of the membrane following the insertion.

The blade member may be provided with a cutting edge on one side and a tongue extension on an opposite side, the tongue extension facilitating a grasping of the blade member and concomitantly the entire device by a grasper instrument during an insertion procedure. The blade member may be further provided with a U-shaped recess in which the proximal flange is seated.

The distal flange may include a pair of flange halves projecting like wings in opposite directions from the tubular member. Preferably, at least one of the flange halves is flexible to facilitate incising of the tympanic membrane by the blade member during an insertion procedure.

Generally, a ventilation or pressure equalization tube with a removable blade member will have an enlargement at the proximal end which serves as a proximal flange, the distal flange and the proximal flange being seated against opposite sides of a tympanic membrane.

A myringotomy ventilation tube in accordance with this embodiment of the present invention represents a considerable advance. A myringotomy and tube placement can be performed more quickly, more safely and with greater ease, inasmuch as the incision and ventilation tube insertion steps are performed by the same instrumentation, namely, the ventilation tube itself.

This technique in accordance with the present invention results in considerable savings inasmuch as reusable or disposable ear drum knives are no longer needed. Such knives are resterilized and stored or thrown away, respectively, after a single operation. Although the ventilation tube in accordance with the invention will be more expensive than a conventional ventilation tube, it is expected that a cost saving will still accrue.

A device for releasing fluid from the middle ear comprises, in accordance with another embodiment of the present invention, a tubular member, a flange connected to one end of the tubular member, and an elongate applicator rod releasably coupled to the tubular member, the applicator rod being provided proximally of tubular member with a blade element. More specifically, the blade element extends substantially transversely to the applicator rod and takes the form of an additional flange extending in a plane oriented substantially transversely to a tubular body portion of the applicator rod, a cutting edge being provided on the additional flange.

In an alternative specific embodiment of the invention, the applicator rod is provided at a distal end with a pair of prongs. The tubular member is mounted to one prong, while the blade element is provided on the other prong.

BRIEF DESCRIPTION OF THE DRAWING

FIG. 1 is side elevational view, on a substantially enlarged scale, of an implant or ventilation tube for use in incising an ear drum in a myringotomy operation and for subsequently serving as a pressure equalization device.

FIG. 2 is a perspective view, on an enlarged scale, of the ventilation tube of FIG. 1.

FIG. 3 is a perspective view, also on an enlarged scale, of the ventilation tube of FIG. 1 connected to the distal end of an applicator rod.

FIG. 4 is a side elevational view, on an enlarged scale, of the applicator rod of FIG. 3, showing a nose extension for releasably coupling the ventilation tube to the application rod.

FIG. 5 is a perspective view, on an enlarged scale, of the ventilation tube of FIGS. 1–3, showing a grasping forceps holding the ventilation tube.

FIG. 6 is a perspective view, on an enlarged scale, of the ventilation tube and grasping forceps of FIG. 5, showing placement or removal of the ventilation tube from an incision formed in an ear drum.

DETAILED DESCRIPTION

Figure 7:
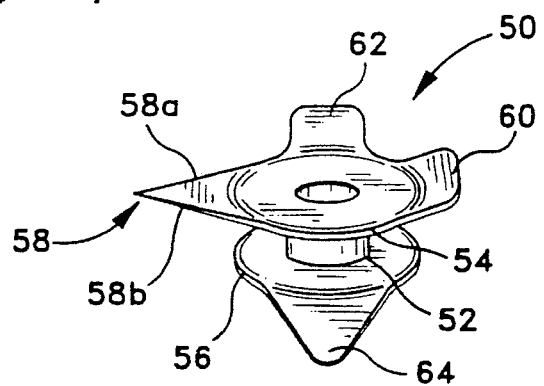
FIG. 7 is a schematic perspective view of another tympanic ventilation or pressure equalization tube with an integral incising edge.

As illustrated in FIGS. 1 and 2, a ventilation tube 10 for use in performing a myringotomy and subsequent pressure equalization comprises a tubular member 12, a first flange or collar 14 connected to a distal end of the tubular member, and a second flange or collar 16 connected to a proximal end of the tubular member. Distal flange 14 is provided along a distal side, i.e., on a side opposite proximal flange 16, with a cutting edge 18 comprising a pair of straight edge segments 18a and 18b oriented at an acute angle with respect to one another to form a cutting wedge extending in a direction away from proximal flange 16.

Ventilation tube 10 further comprises a non-cutting tongue or extension 20 connected to proximal flange 16. Tongue extension 20 projects at a shallow angle from proximal flange 16 on a side thereof opposite distal flange 14.

As depicted in FIG. 3, an elongate applicator rod or obturator 22 is removably coupled to ventilation tube 10 prior to the commencement of a myringotomy. As illustrated in FIG. 4, applicator rod 22 is formed at a distal end with a collar 23 and a distally extending nose portion 24 for releasably holding ventilation tube 10. Nose portion 24 may be inserted into ventilation tube 10 in a loose friction fit.

Applicator rod 22 is made of a material such as a metal or alloy having a limited malleability. Thus, applicator rod 22 may be bent, as shown in FIG. 3, for example, to assume a different configuration prior to the insertion of the rod and ventilation tube 10 into the external auditory canal of a patient. The malleability of applicator rod 22 facilitates the disposition of ventilation tube 10 at an appropriate place in the patient's tympanic membrane.

Ventilation tube 10 can have different dimensions and still be effective for seating in a patient's tympanic membrane. In one configuration, flanges 14 and 16 are approximately three millimeters in diameter, while tubular member 12 has an inner diameter of approximately 1.25 millimeters. Flanges 14 and 16 are spaced from one another by a distance approximately equal to the thickness of a tympanic membrane, for example, approximately 1.55 millimeters.

It is to be noted that applicator rod 22 may be used with conventional ventilation tubes, for example, tubes with flanges or collars, but without cutting edge 18 or tongue extension 20. In such a case, the incision in the patient's tympanic membrane is formed conventionally, with a knife prior to the insertion of the ventilation tube.

In using tympanic ventilation tube 10 and applicator rod 22, ventilation tube 10 is first mounted to the distal end of applicator rod 22. Applicator rod 22 is then manipulated to insert ventilation tube 10 through the patient's auditory canal and to press cutting edge 18 against the tympanic membrane 26 (FIG. 3) so as to form a perforation or incision 28 (FIG. 3) therein. Preferably, upon achieving contact between ventilation tube 10 and the tympanic membrane, applicator rod 22 and concomitantly ventilation tube 10 are pressed towards the drum to facilitate the penetration of the tympanic membrane by cutting edge 18.

Upon penetration of cutting edge 18 through the tympanic membrane 26 to form perforation 28, applicator rod 22 is manipulated to insert distal flange 14 through the perforation, while maintaining proximal flange 16 on the outside of the tympanic membrane. Upon the seating of ventilation tube 10 so that distal flange 14 and proximal flange 16 are disposed on opposite sides of the tympanic membrane, nose portion 24 of applicator rod 22 is removed from ventilation tube 10.

It is to be noted that ventilation tube 10 may be inserted with instrumentation other than applicator rod 22. For example, as depicted in FIGS. 5 and 6, a grasping forceps 30 may be used to press ventilation tube 10 against tympanic membrane 26', to incise perforation 28', to insert distal flange 14 through the perforation or incision, and to seat ventilation tube 10 in the incision. Alternatively, another instrument (not illustrated) which may be used to perform these steps has an inner tube with a distal end insertable into tubular member 12 and further has an outer tube coaxially surrounding the inner tube and slidable in a distal direction with respect thereto to eject ventilation tube 10 from the distal end of the inner tube upon seating of the ventilation tube in the ear drum.

As illustrated in FIG. 7, another tympanic ventilation or pressure equalization tube 50 for ventilating and/or releasing fluid from the middle ear comprises a tubular member 52 provided with a first or proximal flange 54 and a second or distal flange 56 connected to opposite ends of tubular member 52. Proximal flange 54 is provided with a cutting edge 58 comprising a pair of straight edge segments 58a and 58b oriented at an acute angle with respect to one another to form a cutting wedge extending in a lateral or transverse direction away from proximal flange 54.

Figure 8A:
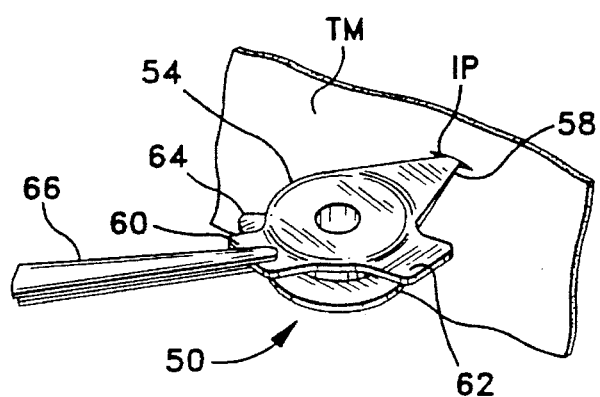
FIGS. 8A–8E are schematic perspective views depicting successive steps in the use of the tympanic ventilation or pressure equalization tube of FIG. 7.
Figure 8B:
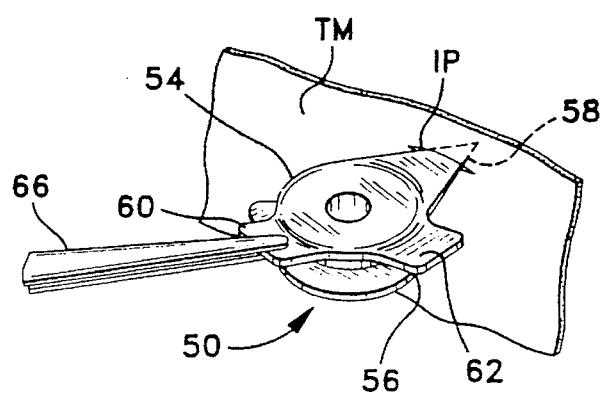
Figure 8C:
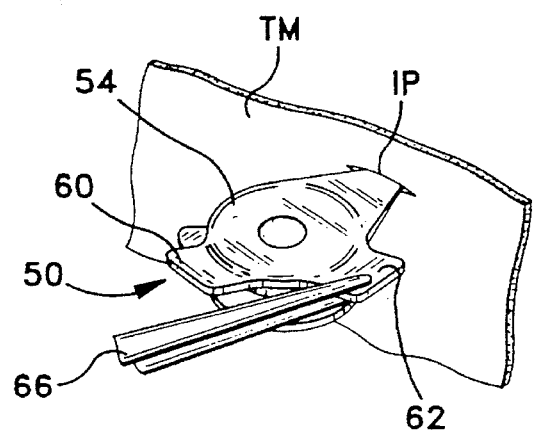
Figure 8D:
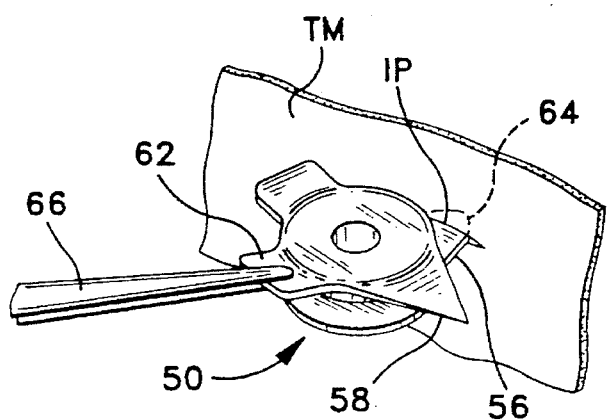
Figure 8E:
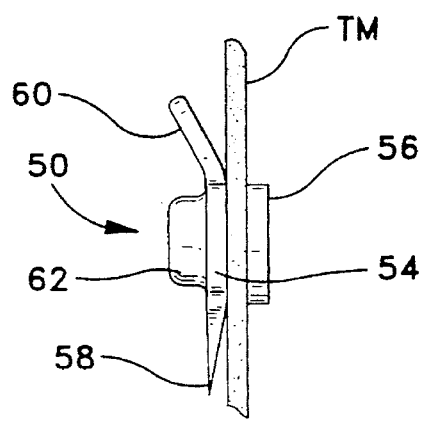

Proximal flange 54 is further provided with a first tongue extension 60 angularly spaced 180° from cutting edge 58 and a second tongue extension 62 angularly spaced 90° from cutting edge 58. Extension 60 facilitates grasping the device to apply pressure through cutting edge 58 to incise the tympanic membrane TM (FIGS. 8A–8E) during an insertion of tubular member 52, while proximal flange 54 and distal flange 56 seat against opposite sides of the membrane following the insertion, as illustrated in FIG. 8E.

Preferably, at least part of distal flange 56 is flexible for facilitating incising and insertion operations, described in detail hereinafter with reference to FIGS. 8A–8E. Flange 56 is also provided with a preferably rigid tongue extension 64 which facilitates insertion of distal flange 56 through an incision or perforation IP (FIGS. 8A–8E) formed in tympanic membrane TM.

In utilizing the tympanic ventilation or pressure equalization tube of FIG. 7 for ventilating and/or releasing fluid from the middle ear, cutting edge 58 is pressed against tympanic membrane TM so as to form incision IP in the membrane. To that end, a grasping forceps 66 is manipulated by the ear surgeon to clamp tongue extension 60 and to incise membrane TM, as illustrated in FIGS. 8A and 8B. FIG. 8B shows a later stage in the incising procedure, wherein distal flange 56 bends against tympanic membrane TM in response to the pressure exerted by the surgeon.

Upon formation of incision or perforation IP, tongue extension 60 is released, thereby temporarily leaving the ventilation tube held in membrane TM by cutting edge 58. Forceps 66 is then manipulated to grasp tongue extension 62, as illustrated in FIG. 8C, and to pull the ventilation tube in the proximal direction to remove cutting edge 58 from perforation IP. Ventilation tube 50 may then be rolled against tympanic membrane at that juncture to pivot the tube relative to forceps 66 so that forceps 66 grasp tongue extension 62 at the angle illustrated in FIG. 8D.

Alternatively, upon formation of incision or perforation IP, tongue extension 60 is used to pull cutting edge 58 from incision IP and to place ventilation tube 50 upon tympanic membrane TM. Forceps 66 is then manipulated to grasp tongue extension 62 at the angle illustrated in FIG. 8D.

Upon the removal of cutting edge 58 from incision IP and the grasping of tongue extension 62 at a suitable angle, forceps 66 is used to move tongue extension 64 of distal flange 56 through incision IP (FIG. 8D), while maintaining proximal flange 54 on an outer side of tympanic membrane TM to thereby dispose the tube in the membrane so that flanges 54 and 56 are seated against opposite sides of membrane TM, as illustrated in FIG. 8E. During the insertion of distal flange 56 through incision IP, that flange may distort slightly, owing to its inherent flexibility, to facilitate the insertion procedure.

The tympanic ventilation or pressure equalization tube of FIG. 7 and the associated method described above with reference to FIGS. 8A–8E serve to place the cutting edge 58 on the outer side of tympanic membrane TM, thereby reducing the chances of possible damage to organs of the middle ear.

As illustrated in FIGS. 9–13, another tympanic ventilation or pressure equalization tube comprises a tapered tubular member 72 and a distal flange 76 including a pair of wing-like flange halves or tabs 74a and 74b projecting in opposite radial directions from one end of the tubular member 72. An annular proximal flange 76 is connected to an opposite end of tubular member 72. Flange 76 has a pair of parallel annular flange parts 76a and 76b which are longitudinally or axially spaced from one another to define an annular groove 78. A blade member 80 is removably attached to proximal flange 76. To that end, blade member 80 is inserted into groove 78. Blade member 80 facilitates the incising of the tympanic membrane during the insertion of tubular member 72, wherein flange halves 74a and 74b and proximal flange 76 seat against opposite sides of the membrane following the insertion.

As illustrated in FIGS. 9–12, blade member 80 includes a straight cutting edge 82 on one side and, on an opposite side, a tongue 84 turned in the proximal direction. Tongue 84 is grasped by a grasping instrument to press cutting edge 82 against a tympanic membrane during a beginning phase of a tube placement operation.

Blade member 80 is further provided with a U-shaped recess 86 which is received into groove 78. In a central region opposite recess 86, blade member 80 is formed with a bulge 88 for facilitating the grasping of blade 80 and the removal thereof following insertion of tubular member 72 into a patient's tympanic membrane.

Distal flange halves 74a and 74b and possibly a portion, if not all, of tubular member 72 is flexible. This flexibility facilitates incising of a tympanic membrane by blade member 80 during an insertion procedure.

Figure 9:
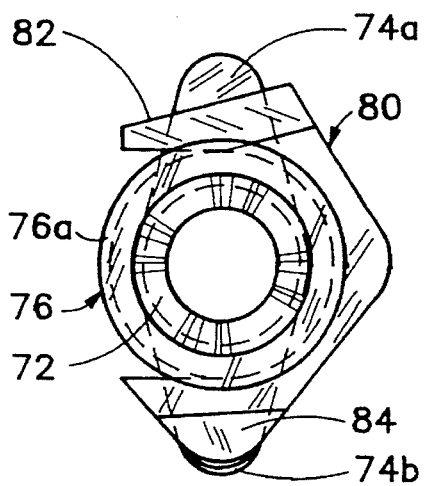
FIG. 9 is a top or proximal side view of a tympanic ventilation or pressure equalization tube.
Figure 11:
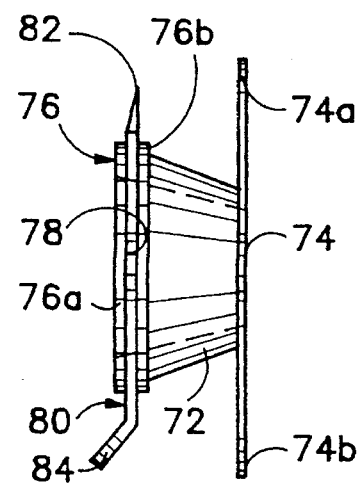
FIG. 11 is a side elevational view of the tympanic ventilation or pressure equalization tube of FIGS. 9 and 10.
Figure 10:
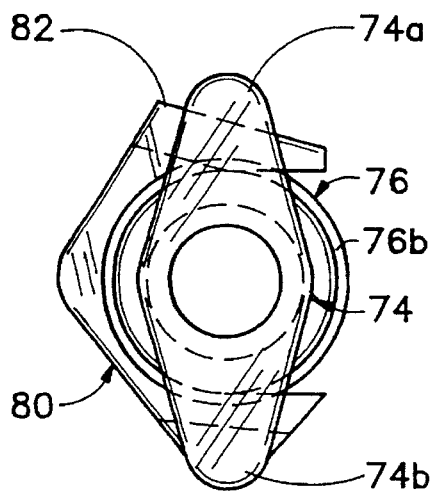
FIG. 10 is a bottom or distal side view of the tympanic ventilation or pressure equalization tube of FIG. 9.
Figure 12:
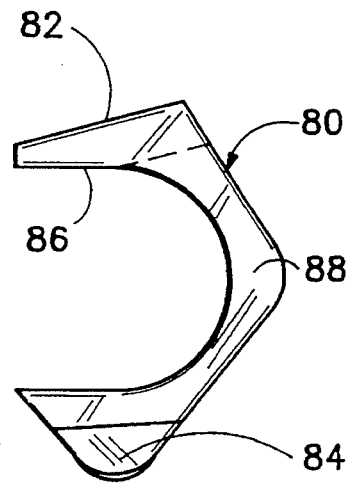
FIG. 12 is a top or proximal side view of a blade member of the tympanic ventilation or pressure equalization tube of FIGS. 9–11.
Figure 13:
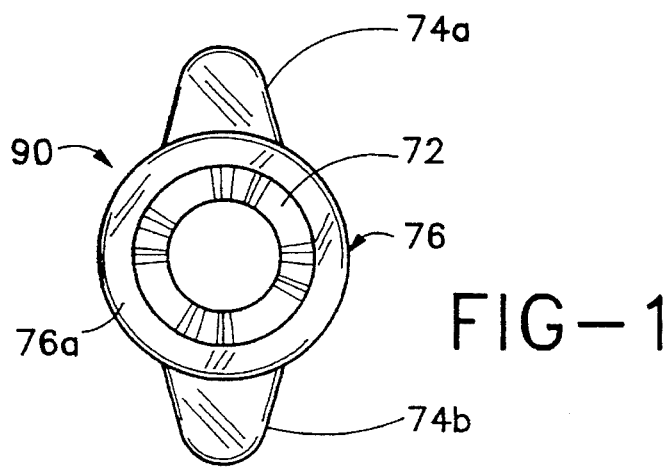
FIG. 13 is a top or proximal side view of a tube portion of the tympanic ventilation or pressure equalization tube of FIGS. 9–11.

In placing a tube portion 90 (FIG. 13) of the tympanic ventilation or pressure equalization tube of FIGS. 9–11, cutting edge 82 of blade member 80 is pressed against a tympanic membrane so as to form a perforation in the membrane. As described above, a grasping instrument (not shown) is used to hold the tube at tongue 84 of blade member 80. Upon formation of a perforation and subsequent removal of cutting edge 82 from the perforation, distal flange half 74a is moved through the perforation, while maintaining proximal flange 76 and blade member 80 on an outer side of the tympanic membrane, thereby seating the tube assembly in the tympanic membrane. Upon seating of the tube assembly in the membrane, blade member 80 is grasped at bulge 88 with the grasping instrument and slid out from groove 78 (FIG. 11) in proximal flange 76. Tube portion 90 (FIG. 13) is left in the membrane.

To move flange half 74a through the perforation or incision in the tympanic membrane, a hold is maintained on tongue 84 by the grasping instrument. Subsequent to the insertion of flange halves 74a and 74b through the perforation, the grasping instrument is moved from tongue 84 to bulge 88.

It is to be noted that blade member 80 may be rotated relative to tube portion 90 prior to the pressing of cutting edge 82 against the tympanic membrane. This procedure enables the surgeon or other user to adjust the position of blade member 80 to facilitate viewing of the distal tabs or flange halves 74a and 74b during the pressing of cutting edge 82 into the tympanic membrane.

It is to be further noted that the incising step is facilitated owing to the flexibility of flange halves 74a and 74b. The pressing of cutting edge 82 against the tympanic membrane is performed in part by bending flange half 74a against the tympanic membrane. However, it is not necessary that the flange halves 74a and 74b are flexible.

It is to be additionally noted that cutting edge 82 is designed to form an incision of a desired length in a tympanic membrane upon pushing of the entire cutting edge through the membrane. This design eliminates the inaccuracies inherent in the estimation technique of conventional tube placement procedures.

Figure 14:
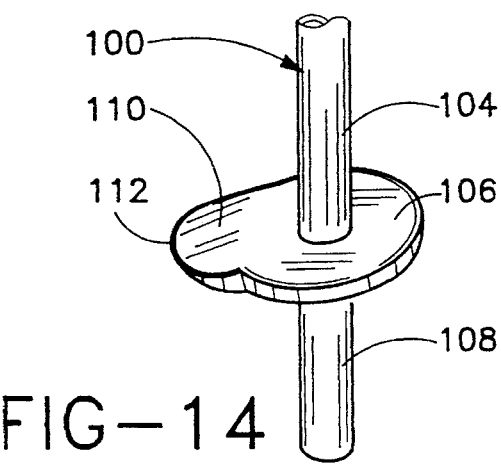
FIG. 14 is a schematic perspective view of an applicator rod for inserting a tympanic ventilation tube.
Figure 15:
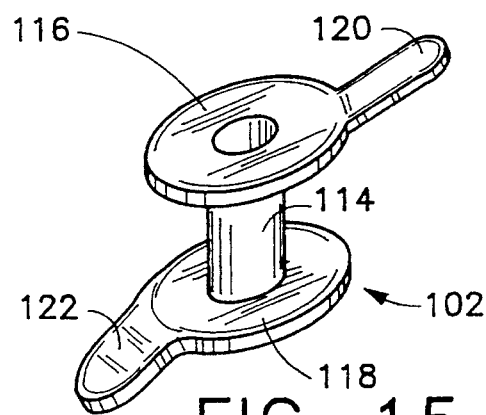
FIG. 15 is a schematic perspective view of a ventilation tube which can be placed in a method using the applicator rod of FIG. 14.

As illustrated in FIG. 14, an applicator rod 100 for use in placing a ventilation tube such as tube 102 of FIG. 15 includes a tubular body portion 104 having a flange 106 spaced from a distal end of the rod to define a distal end portion 108 insertable into tube 102. Flange 106 is a blade member provided with a tongue type extension 110 in turn formed along a radially outer periphery with a cutting edge 112.

As shown in FIG. 15, ventilation or pressure equalization tube 102 includes a tubular member 114, a proximal flange 116 connected to one end of the tubular member and a distal flange 118 connected to an opposite end of the tubular member. Flanges 116 and 118 are provided with respective tongue extensions 120 and 122. Tongue extension 122 on distal flange 118 serves to facilitate the insertion of the distal flange through a perforation 124 in a tympanic membrane TPM (FIG. 17A–17C), while tongue extension 120 on proximal flange 116 may be used to adjust the position of the tube.

Figure 16:
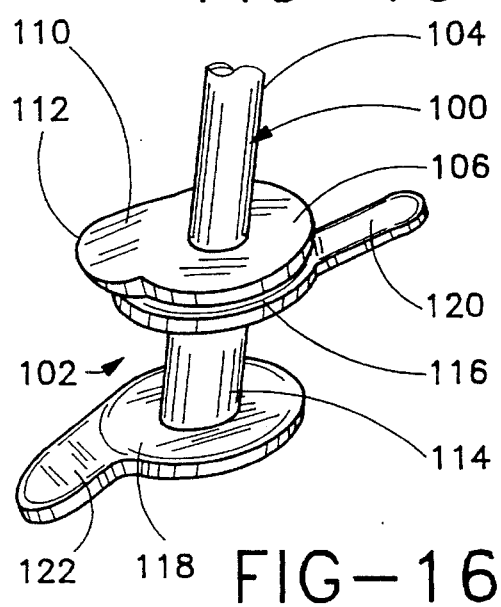
FIG. 16 is a schematic perspective view showing the ventilation tube of FIG. 15 attached to the distal end of the applicator rod of FIG. 14.

As illustrated in FIG. 16, applicator rod 100 is releasably coupled to tube 102 by inserting distal end portion 108 into tubular member 114 so that proximal flange 116 is juxtaposed to blade member 106. Tongue extension 110 and concomitantly cutting edge 112 project beyond proximal tube flange 116.

It is to be noted that tubular member 114 may be tapered like tubular member 72. In that event, distal end portion 108 of rod 100 may be similarly take a frusto-conical form to ensure a sufficiently close fit between tubular member 114 and the applicator rod.

Preferably, at least tongue extension 122, or even the entire distal flange 118 of tube 102 and a portion, if not all, of tubular member 114, is flexible to avoid interference with an incising operation during a pressing of cutting edge 112 into tympanic membrane TPM.

In addition, as discussed above with reference to FIGS. 1–6, applicator rod 100 is made of a material having a limited malleability to facilitate positioning and placement of tube 102.

Figure 17A:
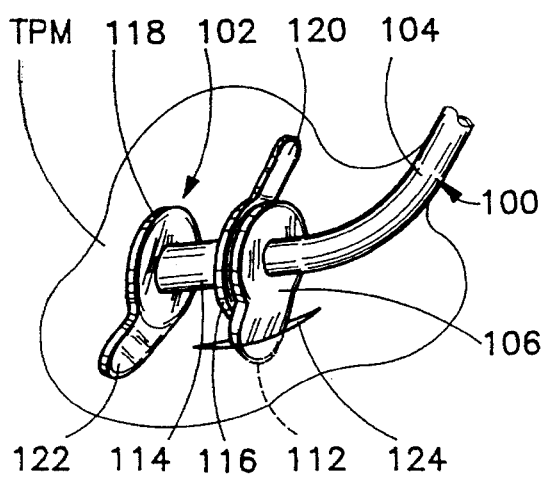
FIGS. 17A–17C are schematic perspective views illustrating successive steps in the use of the applicator rod of FIGS. 14 and 16 to seat the ventilation tube of FIGS. 15 and 16 in a tympanic membrane.
Figure 17B:
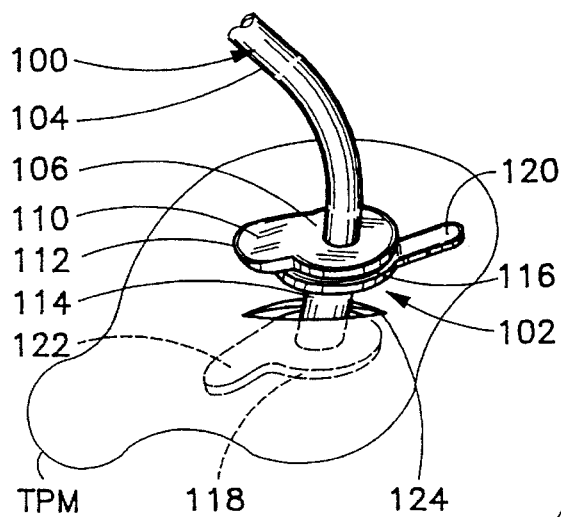

As depicted in FIG. 17A, applicator rod 100 is manipulated to press cutting edge 112 of blade member 106 against tympanic membrane TPM so as to form perforation 124 in the membrane. Subsequently, cutting edge 112 and tongue extension 110 are removed from perforation 124 and rod 100 is manipulated to move first tongue extension 122 and then the entire distal flange 118 of tube 102 through perforation 124, as illustrated in FIG. 17B. Proximal flange 116 and blade member 106 are maintained on an outer side of tympanic membrane TPM, thereby seating tube portion 102 in the membrane. Then, applicator rod 100 and concomitantly blade member 106 are removed from tube 102, while leaving the tube in the tympanic membrane TPM.

As depicted in FIG. 17A, the flexibility of distal flange 118 enables a bending that flange or a portion thereof against tympanic membrane TPM during the pressing of cutting edge 112 through the membrane.

Figure 18:
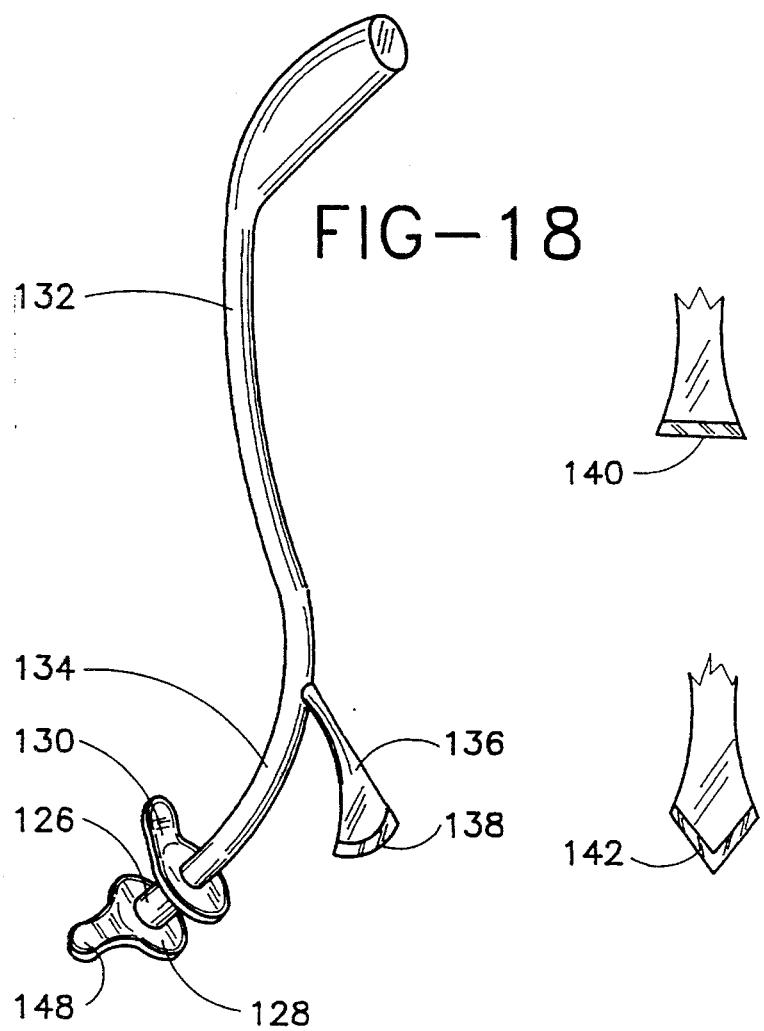
FIG. 18 is a schematic perspective view of another applicator rod and ventilation tube.

As illustrated in FIG. 18, a device or assembly for use in releasing fluid from the middle ear comprises a tubular member 126, a distal flange 128 connected to one end of the tubular member, and a proximal flange 130 connected to an opposite end of the tubular member. An elongate malleable applicator rod 132 is releasably coupled to tubular member 126. More particularly, applicator rod is formed at a distal end with two branches or prongs 134 and 136. A free end of prong 134 is inserted into tubular member 126 and holds the tubular member during an insertion or tube placement procedure. Prong 136 serves as a blade member attached to prong 134 at a point proximal to tubular member 126.

Figure 19:
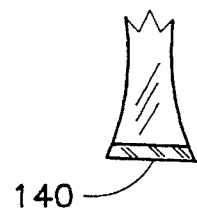
FIGS. 19–21 show respective variations in a cutting edge provided on the application rod of FIG. 18.
Figure 20:
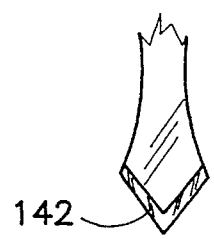
Figure 21:
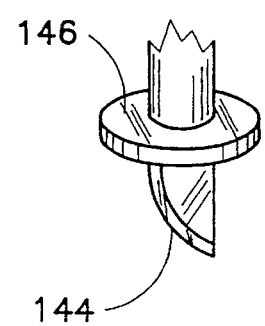

A free end of prong 136 is formed with a cutting or incising edge 138. Alternatively shaped cutting edges 140, 142, and 144 are illustrated in FIGS. 19–21, respectively. Generally, cutting edges 138, 140, 142, and 144 have an effective length, measured transversely to prong 136, which is longer than the diameter of tubular member 126 and shorter than the diameters of flanges 128 and 130. Accordingly, the incising of a perforation in a tympanic membrane by means of cutting edge 138, 140, 142, or 144 will automatically result in an incision of a correct size. In addition, or alternatively, prong 136 may be provided distally of its cutting edge, e.g., edge 144, with an arrest or flange 146 (FIG. 21) for preventing prong 136 from being inserted too far through the tympanic membrane.

Distal flange 128 is provided with a tongue extension 148 serving as an introducer or inserter for facilitating the insertion of distal flange 128 through a tympanic incision formed via cutting edge 138, 140, 142, or 144.

Figure 17C:
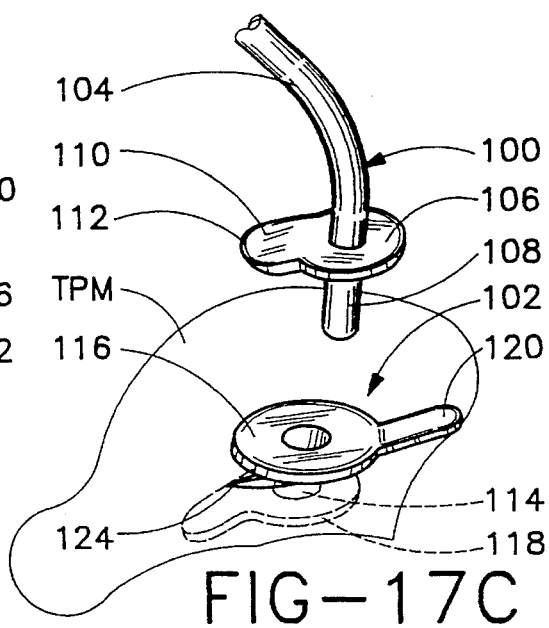

The use of the tube assembly of FIG. 18 in ventilating or equalizing pressure in a patient's middle ear is essentially the same as the procedure described hereinabove with reference to FIGS. 17A–17C. Upon formation of an incision or perforation in a patient's tympanic membrane, applicator rod 132 is manipulated to move tubular member 126 towards the perforation and blade member 138, 140, 142, or 144 away from the perforation.

It is to be noted that all ventilation or pressure equalization tubes described herein have both a distal flange and a proximal flange. In some cases, the proximal flange may be formed by an enlargement of the proximal end of the tubular member, for example, where the tubular member is tapered. The tapering of the tubular member provides the wider, proximal end with the equivalent of a flange.

It is to be further noted that each ventilation or pressure equalization tube described herein may be completely or partially made of a polymeric material impregnated with an antibiotic. Upon implantation or seating of the ventilation or pressure equalization tube in a patient's tympanic membrane, the antibiotic diffuses outwardly from the tube into the tympanic tissues and the middle ear cleft to maintain that region free of any least certain kinds of harmful bacteria.

The antibiotic may be taken from the amino glycocide family, e.g., gentamycin or tobramycin, from the floxin family, the ciprofloxacin family, or from the cephalosporin family. In the embodiments of FIGS. 9 through 18, the entire ventilation tube may be made of a polymeric material impregnated with an antibiotic.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A device for releasing fluid from the middle ear, comprising:

a tubular member;

a distal flange connected to one end of said tubular member;

a proximal flange connected to an opposite end of said tubular member, at least one of said tubular member, said distal flange and said proximal flange being made of a polymeric material impregnated with an antibiotic; and a blade member removably attached to at least one of said tubular member and said proximal flange, said blade member facilitating the incising of a tympanic membrane during an insertion of the tubular member, wherein said proximal flange and said distal flange seat against opposite sides of the tympanic membrane following the insertion.

2. The device defined in claim 1 wherein said blade member extends in a generally lateral direction relative to said tubular member.

3. The device defined in claim 1, further comprising a tongue extension connected to said proximal flange.

4. The device defined in claim 1 wherein said blade member is removably connected to said proximal flange.

5. The device defined in claim 4 wherein said proximal flange has a groove, said blade member being removably inserted into said groove.

6. The device defined in claim 1 wherein said blade member is provided with a cutting edge on one side and a tongue extension on an opposite side, said tongue extension facilitating grasping of said blade member and concomitantly the entire device by a grasper instrument during an insertion procedure.

7. The device defined in claim 1 wherein said distal flange includes a pair of flange halves projecting in opposite directions from said tubular member.

8. The device defined in claim 1 wherein said antibiotic is of the amino glycocide family.

9. The device defined in claim 1 wherein said antibiotic is of the ciprofloxacin family.

10. The device defined in claim 1 wherein said antibiotic is of the floxin family.

11. The device defined in claim 1 wherein said antibiotic is of the cephalosporin family.

12. A device for releasing fluid from the middle ear, comprising:

a tubular member;

a distal flange connected to one end of said tubular member;

a proximal flange connected to an opposite end of said tubular member, at least one of said tubular member, said distal flange and said proximal flange being made of a polymeric material impregnated with an antibiotic; and an elongate applicator rod releasably coupled to a proximal end of said tubular member, said applicator rod being provided proximally of said tubular member with a blade element.

13. The device defined in claim 12 wherein said blade element extends substantially transversely to said applicator rod.

14. The device defined in claim 12 wherein said blade element is an additional flange extending in a plane oriented substantially transversely to a tubular body portion of said applicator rod, a cutting edge being provided on said additional flange.

15. The device defined in claim 12 wherein said applicator rod is provided at a distal end with a pair of prongs, said tubular member being mounted to one of said prongs, said blade element being provided on another of said prongs.

16. The device defined in claim 12 wherein said antibiotic is of the amino glycocide family.

17. The device defined in claim 12 wherein said antibiotic is of the ciprofloxacin family.

18. The device defined in claim 12 wherein said antibiotic is of the floxin family.

19. The device defined in claim 12 wherein said antibiotic is of the cephalosporin family.

* * * * *